(12) United States Patent
Cole-Hamilton et al.

(10) Patent No.: US 7,847,130 B2
(45) Date of Patent: Dec. 7, 2010

(54) IONIC ADDITIVE FOR CATALYSIS IN BIPHASIC REACTION SYSTEMS

(75) Inventors: David Cole-Hamilton, By St. Andrews (GB); Simon Laurent Desset, Woluwe-Saint-Pierre (BE)

(73) Assignee: The University Court of the University of St. Andrews, St. Andrews (GB)

( * ) Notice: Subject to any disclaimer, the term of this patent is extended or adjusted under 35 U.S.C. 154(b) by 0 days.

(21) Appl. No.: 12/438,228

(22) PCT Filed: Aug. 21, 2007

(86) PCT No.: PCT/GB2007/003197

§ 371 (c)(1), (2), (4) Date: May 4, 2009

(87) PCT Pub. No.: WO2008/023171

PCT Pub. Date: Feb. 28, 2008

(65) Prior Publication Data

US 2009/0318734 A1    Dec. 24, 2009

(30) Foreign Application Priority Data

Aug. 21, 2006   (GB)   ................................. 0616486.7

(51) Int. Cl.
  *C07C 45/28*   (2006.01)
  *C07C 5/03*   (2006.01)
  *C09K 3/00*   (2006.01)
(52) U.S. Cl. .................... 568/449; 585/257; 252/182.12
(58) Field of Classification Search .................. 568/449
  See application file for complete search history.

(56) References Cited

U.S. PATENT DOCUMENTS 7,060,860 B2 * 6/2006 Magna et al. ................ 568/454

FOREIGN PATENT DOCUMENTS

DE   3602254 A1   7/1987
EP   0157316 A2   10/1985

OTHER PUBLICATIONS

Pugin et al., Mixtures of Ionic Liquids and Water as a Medium for Efficient Enantioselective Hydrogenation and Catalyst Recycling, 2004, Adv. Synth. Catal., 346(12):1481-1486.
Wolfson et al., The Role of Additional Solvents in Transition Metal Complex Catalyzed Asymmetric Reductions in Ionic Liquid Containing Systems, 2005, J. Organ. Chem., Elsevier-Sequoia S.A., 690(15):3558-3566.
Wolfson et al., Beneficial Effect of Water as Second Solvent in Ionic Liquid Biphasic Catalytic Hydrogenations, 2005, Tetra. Letters, Elsevier Ltd., Amsterdam, 46(14):2513-2516.
Bortolini et al., Sustainable Epoxidation of Electron-Poor Olefins with Hydrogen Peroxide in Ionic Liquids and Recovery of the Products with Supercritical $CO_2$, 2003, Eur. J. Org. Chem., 2003(24):4804-4809.
Mathews et al., N-Donor Complexes of Palladium as Catalysts for Suzuki Cross-Coupling Reactions in Ionic Liquids, 2004, J. Mol. Catalysis A: Chemical, 214(1):27-32.
Liao et al., Ionic Liquid/Water as a Recyclable Medium for Tsuji-Trost Reaction Assisted by Microwave, 2005, Tetra. Letters, 46(20):3469-3472.
Dehmlow, On the Borderline of Aqueous-Phase Catalysis; Phase-Transfer Catalysis, 2004, in *Aqueous-Phase Organometallic Catalysis*, $2^{nd}$ ed., Ch. 4, Cornils et al. eds., Wiley-VCH Verlag GmbH & Co., Weinheim, Germany, pp. 272-312.
Barak et al., Selective Oxidation of Alcohols by a $H_2O_2$-$RuCl_3$ System Under Phase-Transfer Conditions, 1988, J. Org. Chem., 53(15):3553-3555.
Rothenberg et al., Copper-Catalyzed Homolytic and Heterolytic Benzylic and Allylic Oxidation Using *tert*-butyl Hydroperoxide, Jan. 1998, J. Chem., Soc., Perkin Trans., 2:2429-2434.
Wang et al., Kinetic Study of the Phase Transfer Catalytic Epoxidation of Dicyclopentadiene in a Two-Phase Medium, Jan. 2004, Database Compendex [online], Engineering Information, Inc. NY, NY, Database Accession No. E2004078021306, Chem. Eng. Commun., 191(1):27-46 (Abstract).
Kotzabasakis et al., Catalytic Conversions in Aqueous Media: A Novel and Efficient Hydrogenation of Polybutadiene-1, 4-*block*-poly(ethylene oxide) Catalyzed by Rh/TPPTS Complexes in Mixed Micellar Nanoreactors, 2005, J. Mol. Catalysis A: Chemical, 231(1-2):93-101.
Jothimony et al., Mechanism for Transfer Hydrogenation of Ketones to Alcohols Catalysed by Hydridotri-Ironundecacarbonylate Anion Under Phase Transfer Conditions, 1989, J. Mol. Catalysis, 52(2):301-304.
Wolf et al., Palladium-Phosphinous Acid-Catalyzed Sonogashira Cross-Coupling Reactions in Water, 2004, Org. Biomol. Chem., 2(15):2161-2164.
Wolf et al., Efficient Stille Cross-Coupling Reaction Using Aryl Chlorides or Bromides in Water, 2003, J. Org. Chem., 68(19):7551-7554.

(Continued)

*Primary Examiner*—Sikarl A Witherspoon
(74) *Attorney, Agent, or Firm*—Pepper Hamilton LLP (57) ABSTRACT

An additive for improving the rate of catalysis in biphasic reaction systems is disclosed. The additive is an ionic molecule comprising an organic cation such as a heterocyclic compound or a quaternary ammonium or phosphonium cation, and an anion which may be organic or inorganic. A process for improved catalysis in an aqueous biphasic system wherein the catalyst is substantially dissolved in the aqueous phase and the substrate is substantially contained in the non-aqueous phase is also described. A suitable additive is 1-octyl-3-methylimidazolium halide. Examples of suitable catalytic reactions include the hydrogenation, hydrosilation, hydroboration, hydrovinylation, hydroformylation, oxidation and hydroxycarbonylation of alkenes, and Heck, Suzuki, Stille, and Sonogashira coupling.

10 Claims, 3 Drawing Sheets

OTHER PUBLICATIONS

Alonso et al., Non-Conventional Methodologies for Transition-Metal Catalysed Carbon-Carbon Coupling: A Critical Overview, Part I: The Heck Reaction, 2005, Tetrahedron, 61(50):11771-11835.

Zhang et al., Catalysis and Regioselectivity of the Aqueous Heck Reaction by Pd(0) Nanoparticles Under Ultrasonic Irradiation, 2006, J. Org. Chem., 71(11):4339-4342.

Botella et al., Synthesis of Methylated Resveratrol and Analogues by Heck Reactions in Organic and Aqueous Solvents, 2004, Tetrahedron, 60(26):5563-5570.

Bhattacharya et al., Remarkably Facile Heck and Suzuki Reactions in Water Using a Simple Cationic Surfactant and Ligand-Free Palladium Catalysts, 2005, Tetra. Letters, 46(20):3557-3560.

Badone et al., Highly Efficient Palladium-Catalyzed Boronic Acid Coupling Reactions in Water: Scope and Limitations, 1997, J. Org. Chem., 62(21):7170-7173.

Gil-Moltó et al., Di(2-Pyridyl)Methylamine-Palladium Dichloride Complex Covalently Anchored to a Styrene-Maleic Anhydride Co-Polymer as Recoverable Catalyst for C-C Cross-Coupling Reactions in Water, 2005, Tetrahedron, 61(51):12168-12176.

Davis Jr. et al., Synthesis and Purification of Ionic Liquids in *Ionic Liquids in Synthesis*, Wasserscheid et al. eds., Wiley-VCH Verlag GmbH & Co., Weincheim, Germany, 2002, pp. 7-40.

Olivier-Bourbigou et al., Ionic Liquids in Multiphasic Reactions: General Features, Scope, and Limitations in *Ionic Liquids in Synthesis*, Wasserscheid et al. eds., Wiley-VCH Verlag GmbH & Co., Weinheim, Germany, 2002, pp. 258-280.

Holbrey et al, The Phase Behaviour of 1-Alkyl-3-Methlimidazolium Tetrafluoroborates; Ionic Liquids and Ionic Liquid Crystals, *J. Chem. Soc., Dalton Trans.*, 2133-2139, (1999).

\* cited by examiner

IONIC ADDITIVE FOR CATALYSIS IN BIPHASIC REACTION SYSTEMS

The present invention relates to an additive for improving the rate of catalytic reactions in biphasic reaction systems and to the process itself.

Many reactions involve a biphasic reaction system consisting of a water phase containing the catalyst and an organic phase containing the substrate and product. Optionally the organic phase can include an organic solvent.

French patents FR 2,314,910 (1975); FR 2,349,562 (1976); FR 2,338,253 (1976) and FR 2,366,237 (1976) disclose the use of aqueous biphasic systems for catalytic reactions in which the catalyst is rendered soluble in the water phase by the introduction of ionic groups, whilst the substrate and product are substantially immiscible with water. Subsequent developments have been the subject of several reviews (see, for example, E. Weibus and B. Cornils in *Catalyst Separation, Recovery and Recycling: Chemistry and Process Design*, Eds D. J. Cole-Hamilton and R. Tooze, Springer, London, 2006, Chapter 5; *Aqueous-Phase Organometallic Chemistry*, Eds. B. Cornils and W. Herrmann, Wiley VCH, Weinheim, 2004).

Despite the great success that has been achieved with this type of system as a means of separating the products of a reaction from the catalyst and solvent, these systems have generally proved ineffective when long chain alkenes, or other substrates with low water solubility, are employed because very low reaction rates are achieved.

DE 199 25 384 (2000), EP 1,057,524 (2000), DE 199 57 528 (2001), DE 199 57 522 (1999), EP 1,057,538 (2001) and DE 199 08 320 (2000) disclose a rate enhancement for the hydroformylation of long chain alkenes in aqueous biphasic systems of up to 10× by using alternative reactor design and non-standard catalytic conditions.

The use of amphiphilic ligands to enhance the reaction rate is disclosed in *J. Mol. Chem. A*: 1997, 116, 297, *J. Mol. Catal. A*: 1995, 98, 69, *Catal. Today* 1998, 42, 421, *J. Mol. Catal. A*: 2000, 156, 127, *Catal. Letters* 2003, 88, 219, *Adv. Synth. Catal.* 2002, 344, 274. However, catalyst leaching is enhanced and the rate of phase separation is reduced in these methods.

Up to 6 fold enhancement of the hydroformylation rate can be achieved by adding alcohol modifiers, but there is a corresponding loss in selectivity, enhanced catalyst leaching and contamination of the product with alcohols (*Catal. Today*, 1995, 24, 135). The use of cationic surfactants or phase transfer catalysts can enhance the hydroformylation rate by up to 5 fold, but the longer chain surfactants which either have to be added separately (up to 2 fold rate enhancement, EP 157316; *Appl. Catal. A.*: 2003, 242, 85; *J. Mol. Catal. A*: 2002, 189, 195; *J. Mol. Catal.*: 1999, 149, 1; *J. Mol. Catal.* 1978, 4, 315; *Adv. Synth. Catal. A*: 2002, 344, 312; *Adv. Synth. Catal.* 2002, 344, 184; *Appl. Catal. A*: 2002, 236, 173; *Catal. Today* 2003, 79/80, 43; *Appl. Catal. A*: 2002, 225, 239; *J. Mol. Catal. A*: 2003, 200, 157; *J. Mol. Catal. A*: 2002, 189, 195; *J. Mol. Catal. A*: 1999, 149, 1) or as the counterion of an anionic phosphine ligand (up to 5 fold rate enhancement, EP 163234, EP 302375, EP 602463) lead to foaming or emulsification and hence difficult phase separation. Other enhancements can be obtained by using cyclodextrins (*Angew. Chem. Int Ed. Engl.*, 1995, 34, 2269; *J. Mol. Catal. A*, 2000, 176, 105) or thermoregulated ligands which are organic soluble at high temperature but transfer into the water phase on cooling (*Catal. Today*, 1998, 44, 175; *J. Mol. Catal. A*: 1999, 147, 131).

In conclusion, the problem of low reaction rates in aqueous biphasic reaction systems is due to the poor water solubility of the reactants. Attempts to improve the reaction rate by increasing the solubility of the reactants by inclusion of an additive have led to difficulties with separation of the product.

We have now identified additives that provide excellent enhancement of the reaction rate in aqueous biphasic catalysis reaction systems, and which also allow rapid phase separation and low catalyst leaching.

The present invention thus provides a water soluble additive for use in a biphasic reaction system having a water phase containing the catalyst and an organic phase containing the substrate and product. The organic phase can optionally include an organic solvent.

The additive is an ionic molecule, which consists of an organic cation, together with an anion which may be organic or inorganic.

In one embodiment of the invention, the organic cation is a heterocyclic compound having a four to eight membered ring which can be saturated or unsaturated and having one or two heteroatoms (typically nitrogen, oxygen, sulphur or phosphorus) in the ring, and will also be substituted with at least one $C_1$ to $C_{25}$ alkyl chain, optionally branched and/or optionally containing one or more heteroatoms.

The heterocyclic ring will typically consist of 4 to 8 atoms.

In one embodiment the heterocyclic ring is a 5 or 6 membered ring.

In one embodiment the cation is a compound of formula:

wherein $R_1$, $R_2$ and $R_3$ are each independently $C_1$-$C_{25}$ alkyl (preferably $C_4$ to $C_{12}$ alkyl), optionally branched and/or containing one or more heteroatoms. $R_1$ and $R_2$ can be the same or different.

In one embodiment the cation is a compound of formula:

wherein $R_4$ is a $C_{1-10}$ (straight or branched) alkyl chain. In one embodiment $R_4$ is a $C_6$-$C_8$ alkyl chain.

In one embodiment of the invention, the cation can be a quaternary ammonium or phosphonium salt. In general, the N or P atom is attached to at least one alkyl group having more than 4 carbon atoms. The alkyl group can optionally be substituted by groups optionally containing heteroatoms (for example heterocyclic rings).

In this embodiment the cation can be of formula $R_1$-E-$(R_5)_3$ wherein $R_1$ is a $C_1$ to $C_{25}$ alkyl (preferably $C_4$ to $C_{12}$ alkyl), optionally branched and/or containing one or more heteroatoms;

E represents N or P; each $R_5$ independently represents a $C_1$ to $C_8$ alkyl, optionally a $C_1$, $C_2$, $C_3$ or $C_4$ alkyl group.

The additive consists of a cation as described above together with an anion. The anion can be a halide (for example chloride or bromide), sulphate, $BF_4^-$, $CF_3SO_3^-$ or $CF_3CO_2^-$. Other anions that render the additive water soluble can alternatively be used.

In one embodiment the additive is the 1-alkyl-3-methylimidazolium cation with a suitable anion, such as $Cl^-$, $Br^-$, $CF_3SO_3^-$ or $CF_3CO_3^-$. The alkyl group in the cation can be, for example, a $C_6$, $C_7$, $C_8$, $C_9$, $C_{10}$, $C_{11}$, or $C_{12}$ straight or branched alkyl chain.

In one embodiment the additive is the $C_8H_{17}E(CH_2CH_3)_3$ (where E=N or P) cation with a suitable anion, such as $Cl^-$, $Br^-$, $CF_3SO_3^-$ or $CF_3CO_2^-$.

The additive described above is useful in any catalytic reaction involving aqueous biphasic systems in which the catalyst is substantially dissolved in the aqueous phase, whilst the substrate is substantially contained in a separate (non-aqueous, for example organic) phase. This separate phase may consist of the substrate, product and any side products, but could also contain a solvent that is immiscible with water. Non-exclusive examples of suitable catalytic reactions include the hydrogenation, hydrosilation, hydroboration, hydrovinylation, hydroformylation, oxidation and hydroxy-carbonylation of alkenes, Heck, Suzuki, Stille, and Sonigashira couplings, and the like.

The substrates can be any organic compounds that are immiscible with water and are suitable for the reaction. Non-exclusive examples include alkenes with chain lengths of 5 to 50 carbon atoms and containing 1 to 8 double bonds, optionally branched or containing an aromatic ring or heteroatoms. The double bonds may be terminal or internal. Especially preferred substrates are long-chain linear alkenes with 5 to 24 carbon atoms or vinylaromatic compounds. Optionally substituted aromatic compounds can also be substrates.

In a further aspect, the present invention provides a process for improved catalysis of a reaction conducted in an aqueous biphasic system wherein the catalyst is substantially dissolved in the aqueous phase and the substrate is substantially contained in the non-aqueous phase, characterised in that a water soluble additive as described above is added to the reaction mixture.

In one embodiment the chemical reaction is hydrogenation of alkenes.

In one embodiment the chemical reaction is hydroformylation of alkenes.

In one embodiment the chemical reaction is hydroxycarbonylation of alkenes.

In one embodiment the additive is 1-octyl-3-methylimidazolium bromide.

The present invention will now be further described with reference to the following, non-limiting, examples and figures in which.

Figure 1:
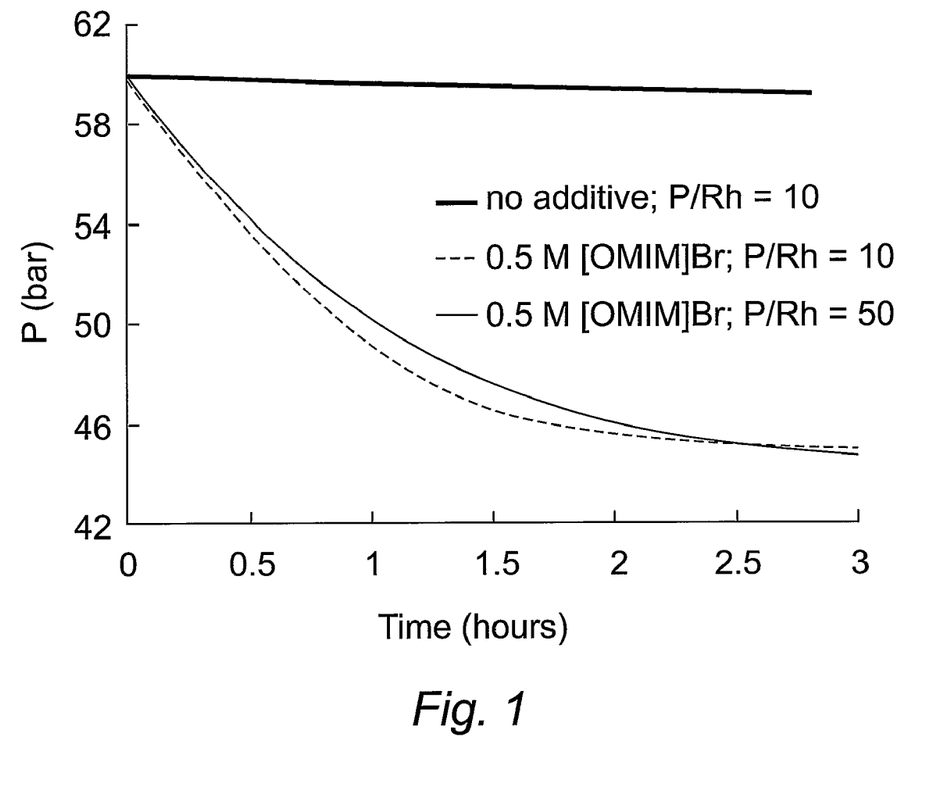
FIG. 1 is a graph showing the effect of [OMIM]Br and different P/Rh ratios on the gas uptake from a ballast vessel during the aqueous-biphasic hydroformylation of 1-octene.
Figure 2:
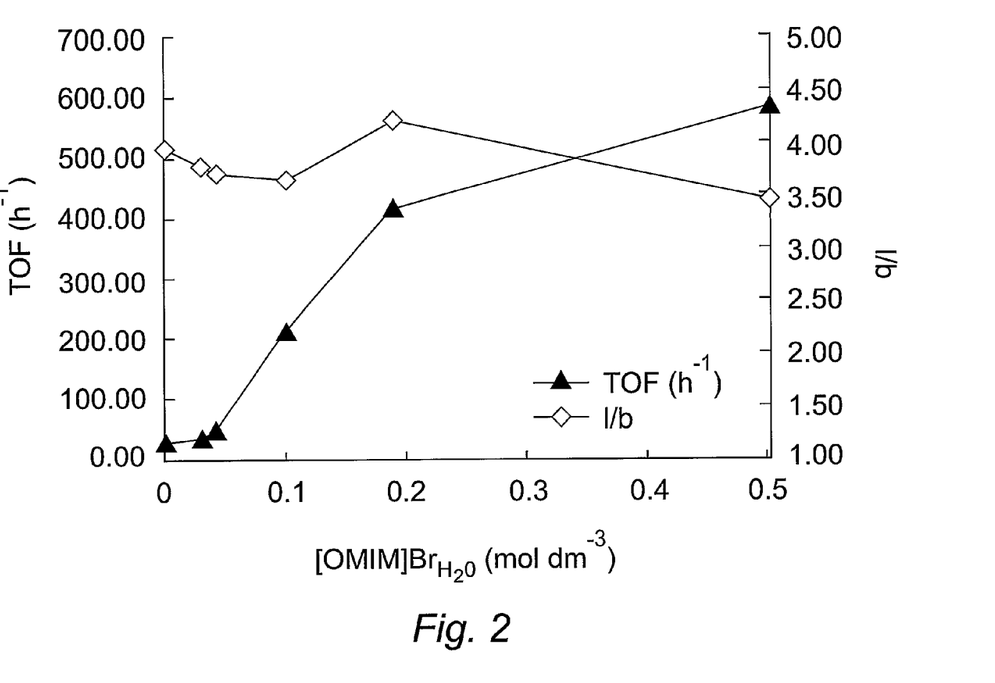
FIG. 2 is a graph showing the effect of the concentration of [OMIM]Br on the average turnover frequency (TOF) and the linear/branched ratio (l/b) for the hydroformylation of 1-octene.
Figure 3:
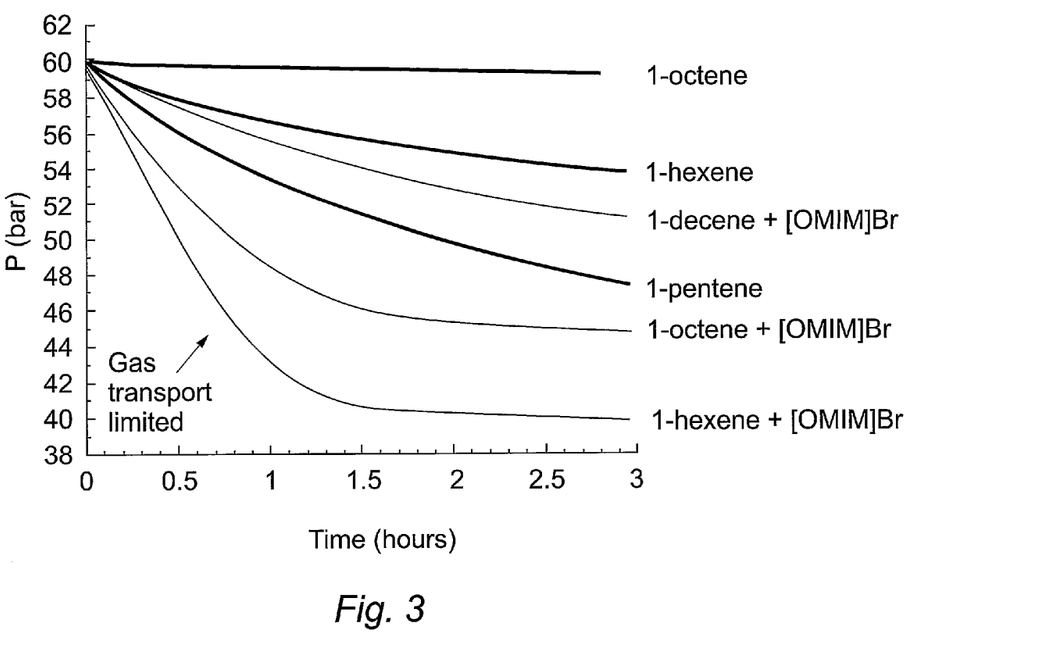
FIG. 3 is a graph showing gas uptake for a variety of alkenes in the presence and absence of added [OMIM]Br.

[Rh(acac)(CO)$_2$] (acacH=2,4-pentane dione) was obtained commercially.

TPPTS (P(3-$C_6H_4SO_3Na)_3$ was prepared by the method described in *Inorganic Synthesis*, 1998, 32, 14.

1-Octyl-3-methylimidazolium bromide [OMIM]Br, 1-hexyl-3-methylimidazolium bromide, [HMIM]Br, and 1-decyl-3-methylimidazolium bromide, [DecMIM]Br, were prepared as follows:

In a round-bottom flask equipped with a magnetic stirrer, a dry nitrogen inlet and a reflux condenser topped with a nitrogen bubbler, N-methylimidazole (20 cm$^3$, 20.6 g, 0.251 mol), one of 1-bromohexane (38.7 cm$^3$, 45.6 g, 0.276 mol), 1-bromooctane (47.7 cm$^3$, 53.3 g, 0.276 mol) or 1-bromodecane (57.3 cm$^3$, 61.1 g, 0.276 mol), and ethylacetate (50 cm$^3$) were introduced. The homogeneous solution was heated under reflux for 14 hours. The biphasic system obtained was separated and the lower viscous product phase was washed with ethylacatate (3×50 cm$^3$). The product was dried in vacuo (0.1 mbar, 5 hours, 50° C.) to yield a pale yellow viscous oil.

1-Octyl-3-methylimidazolium chloride, [OMIM]Cl.

In a round-bottom flask equipped with a magnetic stirrer, a dry nitrogen inlet and a reflux condenser topped with a nitrogen bubbler, N-methylimidazole (20 cm$^3$, 20.6 g, 0.251 mol), 1-chlorooctane (47 cm$^3$, 41.1 g, 0.276 mol) and ethylacetate (50 cm$^3$) were introduced. The homogeneous solution was heated under reflux for 3 days. The biphasic system obtained was separated and the lower viscous product phase was washed with ethylacetate (3×50 cm$^3$). The product was dried in vacuo (0.1 mbar, 5 hours, 50° C.) to yield a pale yellow viscous oil (41.1 g, 71%).

1-Octyl-3-methylimidazolium trifluoroacetate, [OMIM]TFA.

1-octyl-3-methylimidazolium bromide (8.02 g, 0.029 mol), dissolved in distilled water (65 cm$^3$), was added to a suspension of silver trifluoroacetate (6.43 g, 0.029 mol) in distilled water (65 cm$^3$). The suspension was stirrer for 1 hour at 70° C. The silver bromide precipitate was filtered over celite and the water evaporated. The residue was dissolved in methanol and filtered over celite. The methanol was evaporated and the product analysed for remaining bromide; addition of 0.1 mol cm$^{-3}$ aqueous AgBF$_4$ showed no sign of AgBr precipitation. The product was dried in vacuo (0.1 mbar, 50° C., 5 hours) to yield a pale yellow oil (6.61 g, 73.6%).

$\delta_H$ (400 MHz; CDCl$_3$; Me$_4$Si) 0.81 (3H, t, $^3$J 6.9, NC$_7$H$_{14}$CH$_3$), 1.27 (10H, m, CH$_2$), 1.88 (2H, pent, $^3$J 7.2, NCH$_2$CH$_2$), 4.04 (3H, s, NCH$_3$), 4.24 (2H, t, $^3$J 7.4, NCH$_2$), 7.27, 7.33 (2H, 2×t, $^3$J 1.7, NC(H)C(H)N) and 10.36 (1H, s, NC(H)N).

N-Octyl-N,N,N-triethylammonium bromide, [OctNEt$_3$]Br.

In a round-bottom flask equipped with a magnetic stirrer, a dry nitrogen inlet and a reflux condenser topped with a nitrogen bubbler, triethylamine (20 cm$^3$, 14.5 g, 0.143 mol), 1-chlorooctane (25 cm$^3$, 27.9 g, 0.145 mol) and acetonitrile (50 cm$^3$) were introduced. The homogeneous solution was heated under reflux for 14 hours. The product was precipitated by addition of ethylacetate at 5° C. The precipitate was then recrystallized from ethylacetate (36.7 g, 87.3%).

$\delta_H$ (300 MHz; CDCl$_3$; Me$_4$Si) 0.81 (3H, t, $^3$J 6.7, NC$_7$H$_{14}$CH$_3$), 1.20 (10H, m, CH$_2$), 1.32 (9H, t, $^3$J 6.7, NCH$_2$CH$_3$), 1.63 (2H, m, NCH$_2$CH$_2$), 3.20 (2H, m, NCH$_2$C$_7$H$_{15}$) and 3.45 (6H, q, $^3$J 7.2, NCH$_2$CH$_3$); m/z 214 (M$^+$, 100%).

N-Octylpyridinium bromide, [OctPyr]Br.

In a round-bottom flask equipped with a magnetic stirrer, a dry nitrogen inlet and a reflux condenser topped with a nitrogen bubbler, pyridine (10 cm$^3$, 9.8 g, 0.123 mol), 1-bromooctane (24 cm$^3$, 26.8 g, 0.138 mol) and ethylacetate (30 cm$^3$) were introduced. The homogeneous solution was heated under reflux for 14 hours. The biphasic system obtained was separated and the lower viscous product phase was washed with ethylacetate (3×30 cm$^3$). The product was dried in vacuo (0.1 mbar, 5 hours, 50° C.) to yield a pale orange viscous oil (24.1 g, 71.6%).

$\delta_H$ (300 MHz; CDCl$_3$; Me$_4$Si) 0.68 (3H, t, NC$_7$H$_{14}$CH$_3$), 1.14 (10H, m, CH$_2$), 1.91 (2H, q, NCH$_2$CH$_2$CH$_2$C$_5$H$_{11}$), 4.85 (2H, t, NCH$_2$C$_7$H$_{15}$), 8.06 (2H, t, NCHCHCH); 8.45 (1H, t, NCHCHCH) and 9.49 (2H, d, NCHCHCH).

Catalyst Preparation

A catalytic solution was prepared by stirring [Rh(acac)(CO)$_2$] (3.2 mg, 1.25×10$^{-5}$ mmol) with TPPTS (71.1 mg, 0.125×10$^{-3}$ mol) in degassed water (10 cm$^3$) containing the appropriate additive (concentration shown in Tables 1 to 3) under CO/H$_2$ (1:1, 1 bar) at 60° C. for 1 hour.

The resulting yellow solution was stored under CO/H$_2$ and is subsequently referred to as "the stock catalyst solution".

EXAMPLE 1

The stock catalyst solution (8 cm$^3$, 1×10$^{-5}$ mol Rh) with [OMIM]Br as the additive was transferred into an autoclave which had previously been purged by alternating vacuum and argon (3 times) and a slow stream of argon emanating from it. The catalytic solution was purged 3 times with CO/H$_2$ (1:1, 20 bar). Degassed 1-octene (2 cm$^3$) was added and the autoclave sealed and pressurised with CO/H$_2$ (20 bar). It was heated to 100° C. and stirred at 1000 rpm for 2 hours.

The stirrer was stopped, the autoclave quickly cooled (ice bath) and depressurized and the organic phase analysed for its organic content by gas chromatography (GC). The conversion of octene was 92.9% (average turnover frequency (TOF) =586 mol product (mol Rh h)$^{-1}$) and the l:b ratio was 3.5. The phases were completely separate by the time the autoclave was opened.

COMPARATIVE EXAMPLE 2

Example 1 was repeated but omitting the [OMIM]Br. The conversion was 4.9% (average TOF=30) and the l:b ratio 3.9.

EXAMPLES 3-6

Example 1 was repeated but varying the amounts of [OMIM]Br added as shown in Table 1. The results are presented in Table 1.

TABLE 1

Results obtained for hydroformylation of 1-alkenes with different concentrations of [OMIM]Br.
20 bar$^a$ (CO/H$_2$ = 1:1); 100° C.; 2 hours; [Rh]$_{aq}$ = 1.25 mmol dm$^{-3b}$; P/Rh = 10 (P = TPPTS); alkene = 2 cm$^3$; H$_2$O = 8 cm$^3$.

| Example | Substrate | [OMIM]Br$_{aq}$$^b$ (mol dm$^{-3}$) | OMIMBr/P | Conversion (%) | l:b | Average TOF (h$^{-1}$) |
| --- | --- | --- | --- | --- | --- | --- |
| 1 | 1-octene | 0.5 | 40.00 | 92.9 | 3.5 | 586 |
| 2 | 1-octene | 0 | 0 | 4.9 | 3.9 | 30 |
| 3 | 1-octene | 0.19 | 15.2 | 65.9 | 4.2 | 418 |
| 4 | 1-octene | 0.10 | 8.0 | 34.0 | 3.6 | 213 |
| 5 | 1-octene | 0.04 | 3.3 | 7.9 | 3.7 | 50 |
| 6 | 1-octene | 0.03 | 2.4 | 5.4 | 3.8 | 35 |
| 7 | 1-hexene | 0.18 | 14.7 | 72.8 | 5.3 | 580 |
| 8 | 1-hexene | 0 | 0 | 32.8 | 4.6 | 256 |
| 9 | 1-decene | 0.18 | 14.7 | 29.2 | 3.3 | 154 |
| 10 | 1-decene | 0 | 0 | 1.9 | 3.1 | 10 |

$^a$Closed reactor, the pressure dropped as the gas was consummed during the reaction.
$^b$Concentration in the aqueous phase.

EXAMPLE 7

Example 1 was repeated using 1-hexene as substrate instead of 1-octene and 0.18 mol dm$^{-3}$ of [OMIM]Br. The results are presented in Table 1.

COMPARATIVE EXAMPLE 8

Example 7 was repeated but omitting the [OMIM]Br. The results are presented in Table 1.

EXAMPLE 9

Example 7 was repeated using 1-decene as substrate instead of 1-hexene. The results are presented in Table 1.

COMPARATIVE EXAMPLE 10

Example 9 was repeated but omitting the [OMIM]Br. The results are presented in Table 1.

EXAMPLE 11

An autoclave fitted with mechanical stirrer, thermocouple pocket, pressure transducer and attached to a ballast vessel via a catalyst injector and mass flow controller was degassed by pressurizing three times with CO/H$_2$ and releasing the pressure. The stock catalyst solution (8 cm$^{-3}$, 1×10$^{-5}$ mol Rh) containing [OMIM]Br (0.5 mol dm$^{-3}$) was transferred into the autoclave. The autoclave was pressurized with CO/H$_2$ (1:1, 15 bar) and heated to 100° C. Meanwhile, the substrate injector was charged with 1-octene (2 cm$^3$). Once the reactor had reached 100° C., the substrate was injected using an overpressure of CO/H$_2$ and the pressure brought to 20 bar. CO/H$_2$ was then fed from the ballast vessel so as to maintain the pressure in the autoclave at 20 bar and the pressure in the ballast vessel was monitored electronically. At the end of the reaction (reaction time shown in Table 2), the autoclave was quickly cooled (ice bath) and depressurized and the contents analysed by GC for the organic products and by ICP-MS (for Rh). The phases separated in less than 2 minutes after opening the reactor. The results are shown in Table 2.

COMPARATIVE EXAMPLE 12

Example 11 was repeated but omitting the [OMIM]Br. The results are presented in Table 2.

EXAMPLE 13

Example 11 was repeated but adding excess TPPTS (0.5 mmol). The results are shown in Table 2. Complete phase separation had occurred by the time the autoclave was opened.

EXAMPLE 14

Example 13 was repeated but the reaction was stopped after 1 hour. The results are in shown Table 2. Complete phase separation had occurred by the time the autoclave was opened.

EXAMPLE 15

Example 11 was repeated but excess TPPTS (1.0 mmol) was added. The results are shown in Table 2. Complete phase separation had occurred by the time the autoclave was opened.

EXAMPLE 16

Example 15 was repeated but the reaction was stopped after 1 hour. The results are shown in Table 2. Complete phase separation had occurred by the time the autoclave was opened.

EXAMPLE 17

Example 11 was repeated but using 1-hexene (2 cm$^3$) in place of 1-octene. The results are shown in Table 2.

COMPARATIVE EXAMPLE 18

Example 12 was repeated but using 1-hexene (2 cm$^3$) in place of 1-octene. The results are shown in Table 2.

EXAMPLE 19

Example 11 was repeated but using 1-decene (2 cm$^3$) in place of 1-octene. The results are shown in Table 2.

COMPARATIVE EXAMPLE 20

Example 12 was repeated but using 1-decene (2 cm$^3$) in place of 1-octene. The results are shown in Table 2.

TABLE 2

Results obtained for hydroformylation of alkenes in the presence of [OMIM]Br.
20 bar (Constant throughout reaction, CO/H$_2$ = 1:1); 100° C.; 3 hours;
[Rh]$_{aq}$ = 1.25 mmol dm$^{-3b}$; alkene = 2 cm$^{-3}$; H$_2$O = 8 cm$^{-3}$.

| Example | Substrate | [[OMIM]Br]$_{aq}$[b]/ (mol dm$^{-3}$) | OMIMBr/P | P/Rh | Reaction time (h) | Conversion (%) | l:b | Initial TOF (h$^{-1}$) | Rh$_{leaching}$ (/ppm) |
|---|---|---|---|---|---|---|---|---|---|
| 11 | 1-octene | 0.5 | 40 | 10 | 3 | 94.7 | 2.8 | 784[a] | 126 |
| 12 | 1-octene | 0 | 0 | 10 | 3 | 3.5 | 3.9 | 26 | n.d. |
| 13 | 1-octene | 0.5 | 8 | 50 | 3 | 94.6 | 3.3 | 711 | 0.49 |
| 14 | 1-octene | 0.5 | 8 | 50 | 1 | 41.3 | 3.9 | 613 | 0.09 |
| 15 | 1-octene | 0.5 | 4 | 100 | 3 | 66.9 | 4.2 | 503 | 3.48. |
| 16 | 1-octene | 0.5 | 4 | 100 | 1 | 13.8 | 3.62 | 191 | 0.07 |
| 17 | 1-hexene | 0.5 | 40 | 10 | 3 | 91.7 | 2.8 | 1466 | 27 |
| 18 | 1-hexene | 0 | 0 | 10 | 3 | 37.8 | 3.9 | 319 | n.d. |
| 19 | 1-decene | 0.5 | 40 | 10 | 3 | 77.4 | 2.5 | 341 | 24 |
| 20 | 1-decene | 0 | 0 | 10 | 3 | 0.6 | 3.4 | [c] | n.d. |

[a]The reaction was zero order for a substantial part of the gas uptake;

[b]Concentration in the aqueous phase.

[c]The gas uptake was too slow to measure a rate.

COMPARATIVE EXAMPLE 21

Example 13 was repeated but using hexylmethylimidazolium bromide ([HMIM]Br (0.5 mol dm$^{-3}$). The phases were fully separated by the time the autoclave was opened (10 minutes). The results are shown in Table 3.

COMPARATIVE EXAMPLE 22

Example 21 was repeated but using 1-hexene (2 cm$^{-3}$) as substrate. The phases were fully separated by the time the autoclave was opened (10 minutes). The results are shown in Table 3.

COMPARATIVE EXAMPLE 23

Example 13 was repeated but using decylmethylimidazolium bromide

[DecMIM]Br (0.5 mol dm$^{-3}$). The solution appeared as a stable emulsion on opening the autoclave. The results are shown in Table 3.

EXAMPLE 24

Example 11 was repeated but using [OMIM]Cl (0.5 mol dm$^{-3}$). Phase separation was complete on opening the autoclave (less than 10 minutes). The results are shown in Table 3.

EXAMPLE 25

Example 13 was repeated but using [OMIM]Cl (0.5 mol dm$^{-3}$). Phase separation was complete on opening the autoclave (less than 10 minutes). The results are shown in Table 3.

EXAMPLE 26

Example 13 was repeated but using [OctNEt$_3$]Br (0.5 mol dm$^{-3}$). Phase separation was complete on opening the autoclave (less than 10 minutes). The results are shown in Table 3.

EXAMPLE 27

Example 13 was repeated but using [OMIM]TFA (0.5 mol dm-3). Phase separation was complete on opening the autoclave (less than 10 minutes). The results are shown in Table 3.

EXAMPLE 28

Example 27 was repeated but using [OMIM]TFA (0.27 mol dm$^{-3}$). Phase separation was complete on opening the autoclave (less than 10 minutes). The results are shown in Table 3.

EXAMPLE 29

Example 13 was repeated but using [OctPyr]Br (0.5 mol dm$^{-3}$). Phase separation was complete on opening the autoclave (less than 10 minutes). The results are shown in Table 3.

TABLE 3

Results obtained for hydroformylation of alkenes in the presence of different additives.
20 bar (Constant throughout reaction, CO/H$_2$ = 1:1); 100° C.; 3 hours;
[Rh]$_{aq}$ = 1.25 mmol dm$^{-3,a}$, [additive] = 0.5 mol dm$^{-3,a}$;
alkene = 2 cm$^{-3}$; H$_2$O = 8 cm$^{-3}$.

| Example | Substrate | Additive | P:Rh | rate (/s$^{-1}$) | Ald. (/%) | l/b | Initial TOF (h$^{-1}$) | [Rh]$_{org}$ (ppm) |
|---|---|---|---|---|---|---|---|---|
| 21 | 1-octene | [HMIM]Br | 50 | 0.000016 | 11.2 | 8.7 | 57.2 | 0.11 |
| 22 | 1-hexene | [HMIM]Br | 50 | 0.000072 | 36.5 | 13.7 | 222.5 | 0.21 |
| 23 | 1-octene | [DecMIM]Br | 50 | 0.000445 | 96.8 | 3.36 | 1236.6 | 0.39 |
| 24 | 1-octene | [OMIM]Cl | 10:1 | 0.000484 | 95.48 | 3.04 | 1371.6 | 307.0 |
| 25 | 1-octene | [OMIM]Cl | 50:1 | 0.000236 | 93.78 | 3.55 | 694.9 | 20.9 |
| 26 | 1-octene | OctEt$_3$NBr | 50:1 | 0.000107 | 78.4 | 2.94 | 353.13 | 10.1 |
| 27 | 1-octene | [OMIM]TFA | 50:1 | 0.000238 | 82.77 | 3.09 | 654.7 | 0.13 |
| 28 | 1-octene | [OMIM]TFA | 50:1 | 0.000243 | 93.02 | 3.97 | 1181.0 | 3.48 |
| 29 | 1-octene | [OctPyr]Br | 50:1 | 0.0001036 | 6.6 | 3.55 | 64.6 | n.d. |

$^a$Concentration in aqueous phase;
$^b$0.27 mol dm$^{-3,a}$.

The invention claimed is:

1. A biphasic reaction system, said system having
   (i) a water phase containing a catalyst and a water soluble additive, and
   (ii) a non-aqueous phase containing a substrate and a product, and
   wherein the water soluble additive is an ionic molecule consisting of an organic cation together with an anion, wherein the organic cation has the formula:

wherein $R_4$ is a $C_{7-9}$ straight or branched alkyl chain; and wherein the anion is selected from the group consisting of a halide and a sulphate.

2. The biphasic reaction system as claimed in claim 1 wherein the additive comprises a cation selected from 1-heptyl-3-methylimidazolium, 1-octyl-3-methylimidazolium, or 1-nonyl-3-methylimidazolium.

3. A process for catalysis of a reaction conducted in a biphasic system having an aqueous phase and a non-aqueous phase wherein a catalyst is substantially dissolved in the aqueous phase and a substrate is substantially contained in the non-aqueous phase, characterised in that a water soluble additive comprising an ionic molecule consisting of an organic cation together with an anion is added to the reaction, wherein the organic cation has the formula:

wherein $R_4$ is a $C_{7-9}$ straight or branched alkyl chain; and wherein the anion is selected from the group consisting of a halide and a sulphate.

4. The process as claimed in claim 3 wherein the reaction is hydrogenation, hydrosilation, hydroboration, hydrovinylation, hydroformylation, oxidation or hydroxcarbonylation of alkenes.

5. The process as claimed in claim 3 wherein the reaction is hydrogenation of alkenes.

6. The process as claimed in claim 3 wherein the reaction is a Heck, Suzuki, Stille or Sonigashira coupling reaction.

7. The process as claimed in claim 3 wherein the organic cation is 1-heptyl-3-methylimidazolium, 1-octyl-3-methylimidazolium, or 1-nonyl-3-methylimidazolium.

8. The process as claimed in claim 3 wherein the anion is a halide.

9. The biphasic reaction system as claimed in claim 1 wherein the anion is a halide.

10. The process as claimed in claim 3 wherein the reaction is hydroformylation of alkenes.

* * * * *